United States Patent
Rajaram et al.

(10) Patent No.: US 9,056,310 B2
(45) Date of Patent: Jun. 16, 2015

(54) PROCESS FOR THE PREPARATION OF NANOCRYSTALLINE PT—CE OXIDE CATALYST FOR THE SELECTIVE HYDROGENATION OF PHENOL AND ITS DERIVATIVES

(71) Applicant: Council of Scientific & Industrial Research, New Dehli (IN)

(72) Inventors: Bal Rajaram, Dehradun (IN); Sarkar Bipul, Dehradun (IN); Singha Rajib Kumar, Dehradun (IN); Pendem Chandrashekar, Dehradun (IN); Shankha Shubhra Acharyya, Dehradun (IN); Ghosh Shilpi, Dehradun (IN); Goyal Reena, Dehradun (IN); Das Subhasis, Dehradun (IN); Bordoloi Ankur, Dehradun (IN); Konathala Laxmi Narayan Sivakumar, Dehradun (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 14/489,521

(22) Filed: Sep. 18, 2014

(65) Prior Publication Data
US 2015/0080614 A1    Mar. 19, 2015

(30) Foreign Application Priority Data
Sep. 19, 2013 (IN) ............................ 2752/DEL/2013

(51) Int. Cl.
*B01J 23/63* (2006.01)
*C07C 29/20* (2006.01)

(52) U.S. Cl.
CPC .................. *B01J 23/63* (2013.01); *C07C 29/20* (2013.01); *C07C 2101/14* (2013.01)

(58) Field of Classification Search
None
See application file for complete search history.

(56) References Cited

U.S. PATENT DOCUMENTS

| | | | |
|---|---|---|---|
| 2003/0186805 A1* | 10/2003 | Vanderspurt et al. | 502/304 |
| 2003/0235526 A1* | 12/2003 | Vanderspurt et al. | 423/263 |
| 2012/0302437 A1* | 11/2012 | Yang et al. | 502/262 |

OTHER PUBLICATIONS

Database CAPLUS on STN, Acc. No. 2007:1189362, Long et al., Nanotechnology (2007), 18(35), 355601/1-355601/6 (abstract).*
Database CAPLUS on STN, Acc. No. 2005:294226, Liu et al., Beijing Shifan Daxue Xuebao, Ziran Kexueban (2003), 39(6), pp. 780-784 (abstract).*

* cited by examiner

*Primary Examiner* — Brian J Davis
(74) *Attorney, Agent, or Firm* — Frommer Lawrence & Haug LLP; William S. Frommer

(57) ABSTRACT

The present invention provides a process and catalyst for the conversion of phenol and its derivatives to cyclohexane and cyclohexanol. The process provides a direct single step for selective hydrogenation of phenol and its derivatives over Pt—Ce oxide catalyst. The process provides a phenol conversion of 50 to 100% and selectivity of hydrogenated product up to 98%.

12 Claims, 4 Drawing Sheets

PROCESS FOR THE PREPARATION OF NANOCRYSTALLINE PT—CE OXIDE CATALYST FOR THE SELECTIVE HYDROGENATION OF PHENOL AND ITS DERIVATIVES

TECHNICAL FIELD OF THE INVENTION

The invention relates to a process for the preparation of nanocrystalline Pt—Ce oxide catalyst for the selective hydrogenation of phenol and its derivatives. Particularly, the present invention relates to nanocrystalline Pt—$CeO_2$ catalyst obtained from the said process. More particularly, the present invention relates to a process for the liquid phase hydrogenation of phenol and phenolic derivatives over nanocrystalline Pt—$CeO_2$ catalyst.

BACKGROUND AND PRIOR ART OF THE INVENTION

The industrial revolution of fossil fuel provided mankind with cheap and accessible energy and fuels. The demands for the fossil based fuels are immerging constantly, owing to the population growth and improvement of life style. But as the petroleum reserves are diminishing constantly, researchers have been readily diverted to utilize renewable biogenic source of energy and fuels. As the innovation in renewable energy; fuel generation form the renewable sources e.g. biodiesel are taking the spotlight of new generation fuel alternative hence the up-gradation of this bio base oil is of tremendous commercial and industrial interest. So, a numbers of effort are made to improve the quality of bio-oil, implies hydrogenation, FCC, isomerization etc.

Bio-oil is basically made up by the component from cellulose, lignin etc. but in order to use as a suitable fuel, it need to be hydrogenated to bust-up the H/C ratio, octane number, calorific value etc. Owing to this, hydrogenation of phenol and phenolic derivatives has paid much attention over a couple of years. As the bio-oil contains high concentration of water so dehydration catalyst should work in both polar as well as nonpolar medium or in biphasic system.

The selective hydrogenation of phenol or phenolic derivatives to its hydrogenate products also have tremendous commercial interest because of the value addition of bio-oil or subsequent synthesis of cyclohexanol and subsequently to produce adipic acid or caprolactum. So the selective hydrogenation of phenol and its derivatives will be the viable process to upgrade the bio-oil and at the same time cyclohexanol and its derivatives can be produced from phenol and its derivatives. The current industrial process for the production of cyclohexanol from cyclohexane produce low yield with vigorous reaction condition. So the hydrogenation of phenol to cyclohexanol can be an alternative process to produce cyclohexanol. There are reports on the production of cyclohexanol or its derivatives by direct hydrogenation of phenol or its derivatives with such a high yield.

Reference can be made to U.S. Pat. No. 4,503,273 by Phillips Petroleum Company, Okla, where they reported the hydrogenation of phenol and phenolic derivatives for the production of useful chemicals. The invention relates to use group VIII metals (namely Ni, Pd, Pt) catalyst with one promoter in organic solvent in presence of a base of about 145-250° C. at 6.8-13.8 MPa $H_2$ pressure. A conversion of 100% of bisphenol was achieved at 200° C. with a selectivity of 75.0-99.9%. But the requirement of high $H_2$ pressure with considerably high temperature make the process costly, other hand the catalyst worked only with organic solvent along with a promoter and base which is also a disadvantage of this process.

Reference can also be made to European patent application EP 1637512 A1, 2006 by Uday Joshi's group to provide a method of hydrogenating phenol, using carbon dioxide and a supported rhodium and/or ruthenium catalyst, to hydrogenate phenol. The drawback of this process is that used 10 Mpa $H_2$ and 10 MPa $CO_2$ pressure. Using such a high pressure required an additional safety arrangement. Moreover, after 2 h reaction 87% cyclohexanol selectivity was obtained at 80° C.

Reference can be made to the article Chem. Commun., 2013, 49, 303-305 in which Duan et al. have shown that Rh—Ni bimetallic catalyst is efficient to convert 54.4% phenol with 71.2 cyclohexanol selectivity. But process is restricted because of the use of cyclohexane as solvent; furthermore the $H_2$ pressure and the reaction time to achieve the conversion and selectivity were also very high.

Reference can also be made to the Chem. Commun., 2004, 930-931, in which Ohde et al. showed the use of palladium and rhodium nanoparticle stabilized in supercritical $CO_2$ for the catalytic hydrogenation of arenes to cyclohexane. They achieved 80-100% arenes conversion with 60-100% product selectivity with the use of different type of plastic supported palladium and rhodium catalyst.

Reference can be made to J. Am. Chem. Soc. 2011, 133, 2362-2365, in which Wang et al. reported the selective hydrogenation of phenolic compound over Pd® carbon nitride in aqueous medium. The disadvantage of the catalyst is the heavy amount of Pd loading; which restrict the catalyst for its industrial use.

Another reference may also be made to Chem. Comm., 2011, 47, 2529-2531 in which hydrogenation of arene was carried out via palladium nanoparticle stabilized by polyvinylpyrrolidone (PVP). A 100% phenol conversion with 99.8% cyclohexanol was achieved at 2 MPa $H_2$ pressure at 60° C. for 2 h. The major drawback of this work is the use of PVP during the reaction; and the separation of PVP from the reaction mixture will be difficult to use this in the industrial level.

Another reference can be made to Chem. Commun., 2008, 999-1001 by Makowski et al. in which they reported the hydrogenation of hydroxy aromatic derivatives over palladium nanoparticle on hydrophilic carbon. They used high amount of Pd (10 wt %) and reaction time was very lengthy (up to 72 h) to get good yield.

OBJECTS OF THE INVENTION

The main object of the present invention is to provide a process for the preparation of nanocrystalline Pt—$CeO_2$ catalyst for the selective hydrogenation of phenol and its derivatives.

Another objective of the present invention is to provide nanocrystalline Pt—$CeO_2$ catalyst obtained from the said process.

Another objective of the present invention is to provide a process to hydrogenate phenol and phenolic derivatives over Pt—$CeO_2$ catalyst to produce cyclohexanol and derivatives of cyclohexanol.

Another objective of the present invention is to provide a process to hydrogenate phenol and phenolic derivatives with $H_2$ in the liquid phase (batch process).

Another object of this invention is to provide a process, which can effective valulize the abundantly available phenol and phenolic derivatives in bio-oil feedstock to upgrade its H/C ratio, octane number and calorific value.

Yet another object of the present invention is to provide a process to deliver a simple catalyst which is reusable after simple washing.

SUMMARY OF THE INVENTION

Accordingly, the present invention provides a process for the preparation of nanocrystalline Pt—Ce oxide catalyst wherein the said process comprising the steps of
a. mixing a salt of Cerium (Ce), a surfactant and water, with constant stirring for 2-4 h at a range of 35-40° C. while maintaining pH in the range of 8-9 to obtain a gel and further solidifying the gel by autoclaving the gel at temperature ranging between 150-180° C. for 7-10 days to obtain a solid;
b. filtering out and washing the solid as obtained in step (a) with ethanol and drying in an oven at a temperature range of 100-120° C. for a period ranging between 6-18 h followed by calcining the dried product at temperature range of 450-750° C. for a period ranging between 4-10 h to obtain Ce oxide;
c. preparing a solution by stirring Ce oxide as obtained in step (b) in ethanol for a period ranging between 30-120 min at temperature ranging between 30-40° C.
d. preparing second solution by stirring ethanol, water, CTAB (cetyltrimethyl ammonium bromide) and platinum (Pt) salt by stirring at temperature ranging between 30-40° C. until the solution becomes homogeneous;
e. mixing solution as prepared in step (d) with the solution as prepared in (c) dropwise and stirring for a period ranging between 30-120 minute at temperature ranging between 30-40° C. followed by adding excess hydrazine and stirring for 1-2 h at 30-40° C. and subsequently evaporating to dryness at 60-100° C. and further drying at 100-120° C. for 4-12 h then calcing in air atmosphere for 4-6 h at 450-750° C. to obtain nanocrystalline Pt—Ce oxide catalyst The invention also provides a nanocrystalline Pt—Ce oxide catalyst, where the particle size of CeO2 lies between 20-50 nm and Pt-species with an average particle size of 1-3 nm with spherical nature, having molecular formula PtO—CeO2 which comprises of 1-4 wt % Pt and 99-96 wt % CeO2 for use in hydrogenation of phenol to obtain cyclohexanol or substituted cyclohexanol.

DETAILED DESCRIPTION OF THE INVENTION

Figure 1:
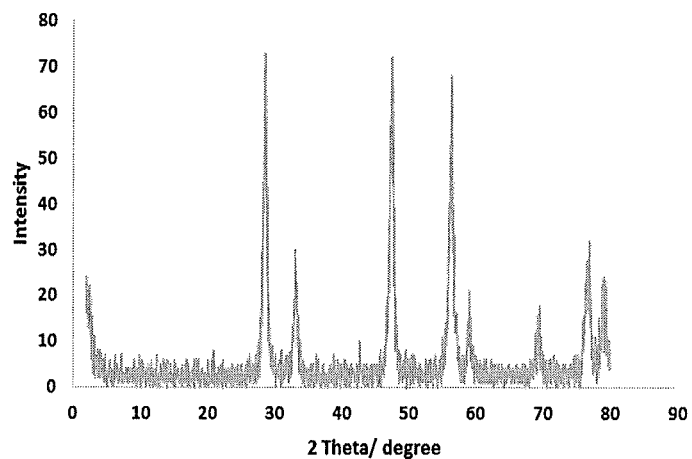
FIG. 1: Powder XRD pattern of 1% Pt—$CeO_2$
Figure 2:
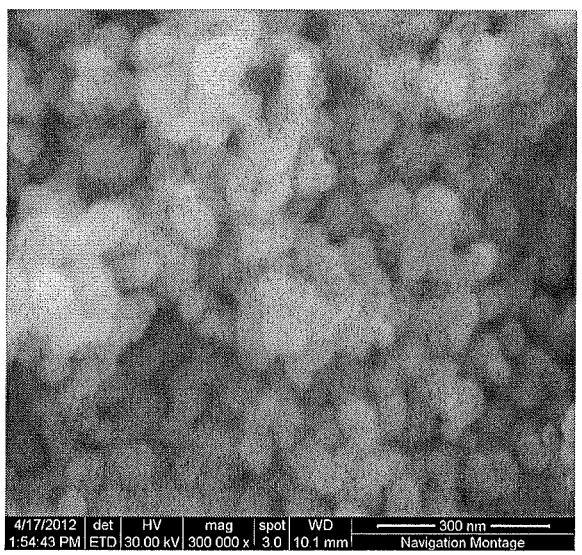
FIG. 2: SEM image of 1% Pt—$CeO_2$
Figure 3:
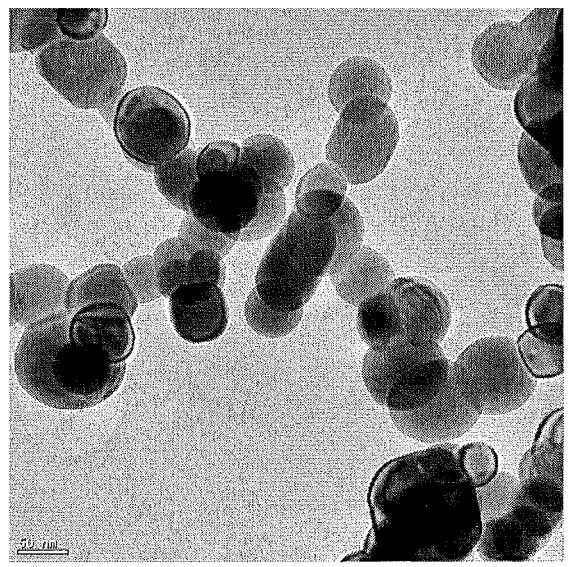
FIG. 3: TEM image of the 1% Pt—$CeO_2$
Figure 4:
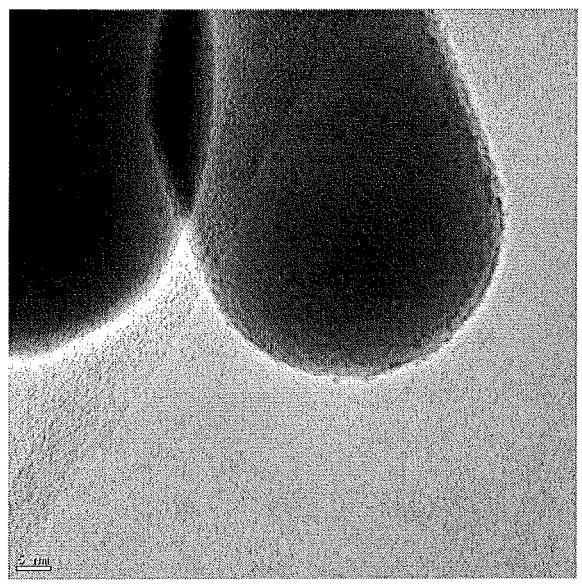
FIG. 4: TEM image of the 1% Pt—$CeO_2$
Figure 5:
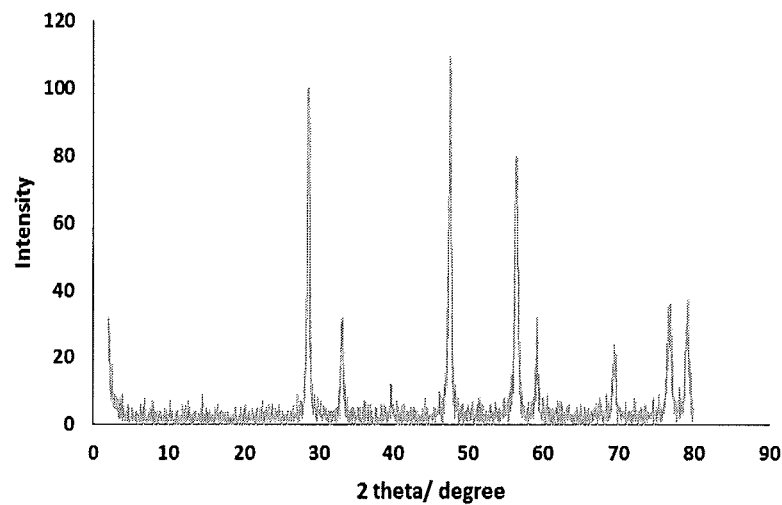
FIG. 5: Powder XRD pattern of 2% Pt—$CeO_2$
Figure 6:
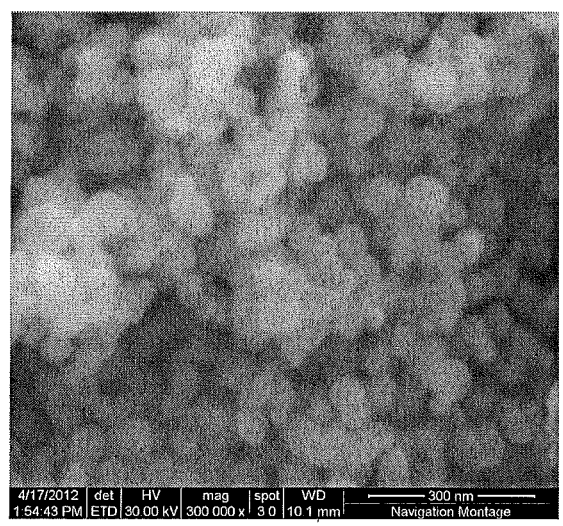
FIG. 6: SEM image of 2% Pt—$CeO_2$
Figure 7:
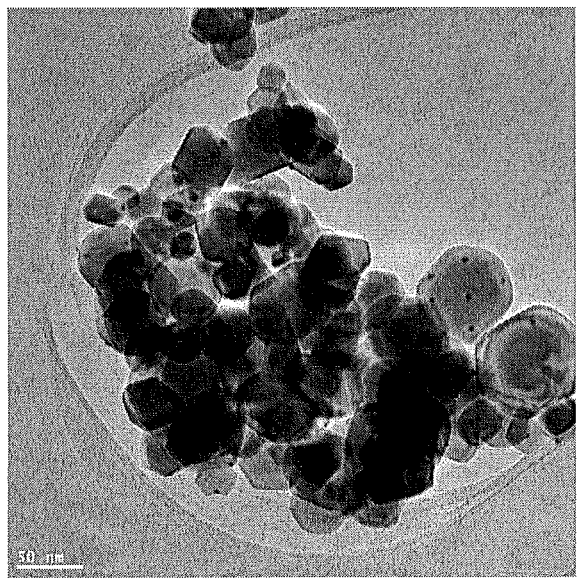
FIG. 7: TEM image of the 2% Pt—$CeO_2$
Figure 8:
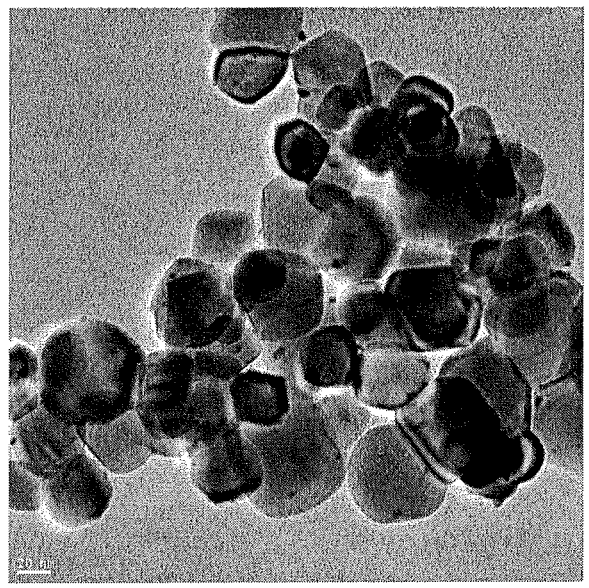
FIG. 8: HRTEM image of the 2% Pt—$CeO_2$

According to an embodiment of the present invention is provided a process for the preparation of nanocrystalline Pt—Ce oxide catalyst and it's use in hydrogenation of phenol.

According to an important embodiment of the present invention is provided a process for the preparation of nanocrystalline Pt—Ce oxide catalyst, wherein the said process comprises the steps of
a. mixing a salt of Cerium (Ce), a surfactant and water, with constant stirring for 2-4 h at a range of 35-40° C. while maintaining pH in the range of 8-9 to obtain a gel and further solidifying the gel by autoclaving the gel at temperature ranging between 150-180° C. for 7-10 days to obtain a solid;
b. filtering out and washing the solid as obtained in step (a) with ethanol and drying in an oven at a temperature range of 100-120° C. for a period ranging between 6-18 h followed by calcining the dried product at temperature range of 450-750° C. for a period ranging between 4-10 h to obtain Ce oxide;
c. preparing a solution by stirring Ce oxide as obtained in step (b) in ethanol for a period ranging between 30-120 min at temperature ranging between 30-40° C.
d. preparing second solution by stirring ethanol, water, CTAB (cetyltrimethyl ammonium bromide) and platinum (Pt) salt by stirring at temperature ranging between 30-40° C. until the solution becomes homogeneous;
e. mixing solution as prepared in step (d) with the solution as prepared in (c) dropwise and stirring for a period ranging between 30-120 minute at temperature ranging between 30-40° C. followed by adding excess hydrazine and stirring for 1-2 h at 30-40° C. and subsequently evaporating to dryness at 60-100° C. and further drying at 100-120° C. for 4-12 h then calcing in air atmosphere for 4-6 h at 450-750° C. to obtain nanocrystalline Pt—Ce oxide catalyst.

In another embodiment of the process for the preparation of nanocrystalline Pt—Ce oxide catalyst, the salt of Ce, surfactant and water in step (a) are mixed in mol ratio range of 1:0.00008:20 to 1:0.00013:30 with constant stirring for 2-4 h preferably at 40° C.

In yet another embodiment of the process for the preparation of nanocrystalline Pt—Ce oxide catalyst, the salt of Ce, surfactant and water in step (a) are preferably mixed in mol ratio of 1:0.0001:24.78.

In another embodiment of the process for the preparation of nanocrystalline Pt—Ce oxide catalyst, the Ce salt used in step (a) is selected from various Ce salt like $Ce(NO_3)_3.6H_2O$ etc.

In an embodiment of the present invention surfactant used in step (a) for the preparation of nanocrystalline Pt—Ce oxide catalyst, is Poly(diallyldimethylammonium chloride) solution (PDADMAC).

In another embodiment of the present invention for the preparation of nanocrystalline Pt—Ce oxide catalyst, Pt to $CeO_2$ is in the range between 1 to 4%.

Still in another embodiment of the present invention for the preparation of nanocrystalline Pt—Ce oxide catalyst, molar ratio of Pt to CTAB in step (d) is in the range of 0.75-1.3.

Still in another embodiment of the present invention for the preparation of nanocrystalline Pt—Ce oxide catalyst, molar ratio of Pt to hydrazine is in the range of 0.75-4.

The present invention provides a process for the preparation of Pt—Ce oxide (Pt nanoparticles supported on $CeO_2$ nanoparticles) to upgrade bio-oil, by aqueous phase hydrogenation of phenol and phenolic derivatives using $H_2$ pressure comprises placing pre-reduced nanocrystalline Pt—Ce oxide catalyst at 5-10% $H_2$ flow at 450-550° C. for 1-2 h, water and phenol or substituted phenol substrate wherein substrate to catalyst weight ratio varies between 100 to 1000 in a batch reactor followed by pressurizing the reactor with $H_2$ at pressure in the range of 1-3 MPa at temperature ranging between 100-200° C. for a period ranging between 1-3 h to obtain cyclohexanol or substituted cyclohexanol.

The process for the preparation of Pt—$CeO_2$ oxide catalyst comprising the steps of:
Synthesis of $CeO_2$ oxide was carried out using gel composition of $Ce(NO_3)_3.6H_2O$, Poly(diallyldimethylammonium chloride) solution (PDADMAC), 25% $NH_3$ solution where $Ce(NO_3)_3.6H_2O$ is the precursor of Ce.

The molar ratio of Ce to PDADMAC varied in the range of 8000-12000

The molar ratio of $H_2O$ to Ce varied in the range of 200-300

The mixing gel is stirred for 2-6 h at room temperature.

Heating of the resultant solution is done in a closed autoclave at 180° C. for 8-10 days.

The product is filtered with excess water and dried in an oven with temperature range of 100-120° C. for 3-24 h. The dried product was calcined in a furnace in the temperature range of 400-750° C. for 3-10 h.

Pt was incorporated with the above prepared $CeO_2$ using bi-solvation method; solution 1 consist required amount of $[Pt(NH_3)_4](NO_3)_2$ dissolved in a water-ethanol medium with cetyltrimethylammonium bromide. Solution 2 containing measured amount of previously prepared $CeO_2$ is taken with 30 ml of ethanol and stirred. Then solution 1 is added to solution 2 drop-wise and the resultant mixture is reduced with excess hydrazine.

The wt. % of Pt supported on nanocrystalline $CeO_2$ varies in the range of 1 to 5.

Calcination of the materials is done in the temperature range of 450-750° C. for 3-6 h.

Still in another embodiment of the present invention is provided nanocrystalline Pt—Ce oxide catalyst, where the particle size of CeO2 lies between 20-50 nm and Pt-species with an average particle size of 1-3 nm with spherical nature catalyst obtained from the process as claimed in claim 1 having molecular formula $PtO$—$CeO_2$ which comprises of 1-4 wt % Pt and 99-96 wt % $CeO_2$.

Still in another embodiment of the present invention a process for hydrogenation of phenol using nanocrystalline Pt—Ce oxide catalyst as obtained in process comprises placing pre-reduced nanocrystalline Pt—Ce oxide catalyst at 5-10% $H_2$ flow, water and phenol or substituted phenol substrate at 450-550° C. for 1-2 h, wherein substrate to catalyst weight ratio varies between 100 to 1000 in a batch reactor followed by pressurizing the reactor with $H_2$ at pressure in the range of 1-3 MPa at temperature ranging between 100-200° C. for a period ranging between 1-3 h to obtain cyclohexanol or substituted cyclohexanol Still in another embodiment of the present invention conversion of phenol or substituted phenol is in the range of 50-100%.

Still in another embodiment of the present invention selectivity of cyclohexanol or substituted cyclohexanol is in the range of 63-100%.

General Procedure for the Hydrogenation of Phenol and its Derivatives

The hydrogenation of phenol and phenolic derivatives was carried out in a Parr reactor under 1-3 MPa $H_2$ pressure. Typically 100 mg of catalyst was reduced at 10% $H_2$ flow at 550° C. for 1 h before each reaction. 0.01 mol substrate was taken in 20 ml deionised $H_2O$ and the reactor was pressurised with $H_2$. The reaction products were identified by GC-MS (HP 5890 GC coupled with 5972 MSD) equipped with CP-SIL-5 capillary column and the product was analysed using a gas chromatography (Agilent 7890A) fitted with a FID using HP-5 capillary column.

The reaction temperature is preferably in the range 40-200° C.

The reaction time used is preferably in the range 1-3 h.

The reaction pressure is preferably in the range of 1-3 MPa.

The conversion of phenol and its derivatives is in the range of 50-100%.

The selectivity of cyclohexanol and its derivatives is in the range of 63-100%.

EXAMPLES

The following examples are given by way of illustration of the working of the invention in actual practice and should not be construed to limit the scope of the present invention in any way.

Example-1

An aqueous solution of a given amount of cerium nitrate $(Ce(NO_3)_3.6H_2O, 21.901$ g) was added to vigorously stirred mixture of Poly(diallyldimethylammonium chloride) solution (PDADMAC; 1.73 g) in deionized $H_2O$ (22.5 ml). The pH of the medium was made 9 by adding ammonium hydroxide solution. Then the resultant solution was kept at 40° C. for 2 h and finally the resultant gel was transferred in to a stainless steel line autoclave and kept for 7 days at 180° C. The resultant solid was washed with ethanol, and dried at 110° C., for 24 hours, followed by calcination at 550° C. for 6 hrs.

The impregnation of Pt was done in bi-solvation method. In solution-1; 30 ml ethanol and 5 ml distilled water was taken in a 100 ml beaker, and then 0.007 g CTAB (cetyltrimethyl ammonium bromide) was added to it under stirring. Finally, 0.0086 g platinum salt was added and stirred at 40° C. until the solution becomes homogeneous. Whereas in solution-2; 2 g of previously prepared $CeO_2$ is stirred in 30 ml of ethanol for 30 minutes at 40° C. Finally, solution-1 was added to the solution-2 in drop wise manner and stirred for 30 minutes at 40° C. A large excess hydrazine (0.2 ml) was added for reduction purpose and kept for stirring for 2 h at 40° C. The reagents were added maintaining the following molar ratio:

Pt:CTAB:hydrazine=1:0.75:5.

The content was evaporated to dryness at 60° C. and kept for drying at 120° C. for 6 hrs. Then the material was calcined in air atmosphere at 550° C. for 4 h.

The catalyst can be denoted as 1% Pt—$CeO_2$ [1 (wt %) Pt in $CeO_2$].

Characterisation of the Catalyst

Powder X-Ray Diffraction (XRD)

XRD pattern of 1% Pt—$CeO_2$ shows the main peaks at 28.5, 33.2, 47.6, 56.5, 59.2, 69.8, 76.9 and 79.2° (2θ) are due to the $CeO_2$ support (JCPDS card no-43-1002).

Two diffraction peaks of Pt° at 2θ=39.8 and 46.3° corresponding to the crystal faces of Pt (111) and (200), respectively been found, which coincide well with the literature values (JCPDS No. 87-0646).

Scanning Electron Microscopy (SEM)

SEM image of 1% Pt—$CeO_2$ shows that the sample contain uniform surface of $CeO_2$ with 30-40 nm particle whereas, no Pt was visible catching the possibility of formation of Pt nanocluster supported on $CeO_2$.

Transmission Electron Microscopy (TEM)

TEM microscopic images of the 1% Pt—$CeO_2$ catalyst.

Presences of Pt-species with an average particle size of 1-2 nm were found over the nanocrystalline $CeO_2$.

Example-2

An aqueous solution of a given amount of cerium nitrate $(Ce(NO_3)_3.6H_2O, 21.901$ g) was added to vigorously stirred mixture of Poly(dialtytdimethylammonium chloride) solution (PDADMAC; 1.73 g) in deionized $H_2O$ (22.5 ml). The pH of the medium was made 9 by adding ammonium hydroxide solution. Then the resultant solution was kept at 40° C. for 4 h and finally the resultant gel was transferred in to a stainless steel line autoclave and kept for 7 days at 180° C. The resultant solid was washed with ethanol, and dried at 110° C., for 24 hours, followed by calcination at 550° C. for 6 hrs.

The impregnation of Pt was done in bi-solvation method. In solution-1; 30 ml ethanol and 5 ml distilled water was taken in a 100 ml beaker, and 0.12 g CTAB (cetyltrimethyl ammonium bromide) was added to it under stirring. Finally, 0.0172 g platinum salt was added and stirred until the solution becomes homogeneous at 40° C. Whereas in solution-2; 2 g of previously prepared $CeO_2$ is stirred in 30 ml of ethanol for 30 minutes at 40° C. Finally, solution-1 was added to the solution-2 in dropwise manner and stirred for 30 minutes. A large excess hydrazine (0.4 ml) was added for reduction purpose and kept for stirring for 2 h at 40° C. The reagents were added maintaining the following molar ratio:

Pt:CTAB:hydrazine=1:0.75:5.

The content was evaporated to dryness at 60° C. and kept for drying at 120° C. for 6 hrs. Then the material was calcined in air atmosphere at 550° C. for 4 h.

The catalyst can be denoted as 2% Pt—$CeO_2$ [2 (wt %) Pt in $CeO_2$].

Characterisation of the Catalyst

Powder X-Ray Diffraction (XRD)

XRD pattern of 2% Pt—$CeO_2$ shows the main peaks at 28.5, 33.2, 47.6, 56.5, 59.2, 69.8, 76.9 and 79.2° (2θ) are due to the $CeO_2$ support (JCPDS card no-43-1002). There were only two diffraction peaks of Pt° at 2θ=39.8 and 46.3° corresponding to the crystal faces of Pt (111) and (200), respectively, which coincide well with the literature values (JCPDS No. 87-0646).

Scanning Electron Microscopy (SEM)

SEM image of Pt—$CeO_2$ shows that the sample contain uniform surface of $CeO_2$ with 30-40 nm particle whereas, no Pt was visible catching the possibility of formation of Pt nanocluster supported on $CeO_2$.

Transmission Electron Microscopy (TEM)

TEM microscopic images of the 2% Pt—$CeO_2$ catalyst.

High resolution transmission electron microscopy (HR-TEM) revealed a presence of Pt-species with an average particle size of 2-3 nm homogeneously dispersed over the nanocrystalline $CeO_2$.

Example-3

This example describes the conditions for hydrogenation of phenol by aqueous phase reaction under $H_2$ pressure using Pt supported Ce-oxide as the catalyst. Process conditions Catalyst: Pt supported Ce-oxide 0.1 g (catalyst prepared in Example 2 was used)

Pt:Ce-oxide weight ratio in the catalyst=2:98

Hydrogen pressure: 3 Mpa

Temperature: 200° C.

Reaction time: 3 h

Substrate to catalyst=1:0.1

Product analysis:

Phenol conversion: 100%

Selectivity of cyclohexanol: 98%

Example-4

This example describes the conditions for hydrogenation of phenol by aqueous phase reaction under $H_2$ pressure using different nanocrystalline oxide as the catalyst. (Table-1)

Process conditions

Nanocrystalline Pt supported Ce-oxide Catalyst: 0.1 g

Pressure: 3 MPa $H_2$

Reaction temperature: 200° C.

Reaction time: 3 h

Substrate to catalyst=1:0.1

TABLE 1

| Entry | Catalyst | Active metal | % of loading | Phenol conversion | Selectivity Cyclohexanol | Cyclohexanone |
|---|---|---|---|---|---|---|
| 1 | Pt—$CeO_2$ | Pt | 1 | 50 | 93 | 6 |
| 2 | Pt—$CeO_2$ | Pt | 2 | 100 | 98 | 2 |

Example-5

The example describes the effect of temperature on hydrogenation of phenol and selectivity of cyclohexanol. The product analysis presented in Table-2.

Process Conditions:

Nanocrystalline Pt supported Ce-oxide Catalyst: 0.1 g

Pt:$CeO_2$ wt % in the catalyst=2%

Pressure: 3 MPa $H_2$

Reaction time: 3 h

Substrate to catalyst=1:0.1

TABLE 2

| Entry | Catalyst | % of loading | Temp. (° C.) | Phenol conversion | Selectivity Cyclohexanol | Cyclohexanone |
|---|---|---|---|---|---|---|
| 1 | Pt—$CeO_2$ | 2 | 200 | 100 | 98 | 2 |
| 2 | Pt—$CeO_2$ | 2 | 100 | 100 | 100 | — |
| 3 | Pt—$CeO_2$ | 2 | R.T. | 24 | 100 | — |

Example-6

The example describes the effect of $H_2$ pressure on hydrogenation of phenol and selectivity of cyclohexanol. The product analysis presented in Table 3

Process Conditions:

Catalyst: 0.1 g

Pt:$CeO_2$ wt % in the catalyst=2%

Reaction Temperature: 100° C.

Reaction time: 3 h

Substrate to catalyst=1:0.1

TABLE 3

| Entry | Catalyst | % of loading | H$_2$ pressure (MPa) | Phenol conversion | Selectivity Cyclohexanol | Cyclohexanone |
|---|---|---|---|---|---|---|
| 1 | Pt—CeO$_2$ | 2 | 3 | 100 | 100 | — |
| 2 | Pt—CeO$_2$ | 2 | 2 | 41 | 96.9 | — |
| 3 | Pt—CeO$_2$ | 2 | 1 | 37 | 90.3 | 2.1 |

Note: the products of phenol hydrogenation were obtained as cyclohexanol (major), cyclohexanone and cyclohexane. It is also to note that for entry no 2 and 3 the rest of the selectivity is for cyclohexane formed during the reaction.

Example-7

The example describes the effect of reaction time on hydrogenation of phenol and selectivity of cyclohexanol. The product analysis presented in Table-4.

Process Conditions:
Catalyst: 0.1 g
Pt:CeO$_2$ wt % in the catalyst=2%
H$_2$ Pressure: 3 MPa
Reaction temperature: 100° C.
Substrate to catalyst=1:0.1

TABLE 4

| Entry | Catalyst | % of Loading | Reaction time (h) | Phenol conversion | Selectivity Cyclohexanol | Cyclohexanone |
|---|---|---|---|---|---|---|
| 1 | Pt—CeO$_2$ | 2 | 3 | 100 | 100 | 0 |
| 2 | Pt—CeO$_2$ | 2 | 2 | 85 | 98.5 | 1.5 |
| 3 | Pt—CeO$_2$ | 2 | 1 | 42 | 95 | 5 |

Example-8

The example describes the hydrogenation of phenolic derivatives and selectivity of cyclohexanol derivatives. The product analysis presented in Table-5.

Process Conditions:
Catalyst: 0.1 g
Pt:CeO$_2$ wt % in the catalyst=2%
H$_2$ Pressure: 3 MPa
Reaction temperature: 100° C.
Reaction time: 3 h
Substrate to catalyst=1:0.1

TABLE 4

| Entry | Catalyst | % of loading | Substrate | Phenol conversion | Selectivity | |
|---|---|---|---|---|---|---|
| 1 | Pt—CeO$_2$ | 2 | phenol | 100 | cyclohexanol | cyclohexanone 0 |
| 2 | Pt—CeO$_2$ | 2 | o-cresol | 98.5 | 2-methylcyclohexanol 63 | 2-methylcyclohexanone 33 |
| 3 | Pt—CeO$_2$ | 2 | p-cresol | 95.3 | 4-methylcyclohexanol 69.8 | 4-methylcyclohexanone 27.4 |

Note:
It is to note that for entry no 2 and 3 the rest of the selectivity is for cyclohexanol, cyclohexanone formed during the reaction.

ADVANTAGES OF THE INVENTION

1. The process of the present invention is effect to upgrade bio-oil by hydrogenating phenol and phenolic derivatives in aqueous medium in a single step with a single catalyst.
2. The process provides not only good conversion but also good selectivity for cyclohexanol and substituted cyclohexanol.
3. The process produces 100% cyclohexanol from phenol which is a major advantage of this process.
4. The process does not need any addition reagent (such as chlorine, bromine etc.) or polymeric additives to achieve good conversion.
5. The catalyst is used in very low amounts.
6. The catalyst does not deactivate even after 4 reuse.
7. The ICP-AES confirms no leaching of Pt which endorses true heterogeneity of our catalyst.

We claim:

1. A process for the preparation of nanocrystalline Pt—Ce oxide catalyst wherein the said process comprising the steps of
   (a) mixing a salt of Cerium (Ce), a surfactant and water, with constant stirring for 2-4 h at a range of 35-45° C. while maintaining pH in the range of 8-9 to obtain a gel and further solidifying the gel by autoclaving the gel at temperature ranging between 150-180° C. for 7-10 days to obtain a solid;
   (b) filtering out and washing the solid as obtained in step (a) with ethanol and drying in an oven at a temperature range of 100-120° C. for a period ranging between 6-18 h followed by calcining the dried product at temperature range of 450-750° C. for a period ranging between 4-10 h to obtain Ce oxide;
   (c) preparing a solution by stirring Ce oxide as obtained in step (b) in ethanol for a period ranging between 30-120 min at temperature ranging between 30-40° C.
   (d) preparing second solution by stirring ethanol, water, CTAB (cetyltrimethyl ammonium bromide) and platinum (Pt) salt by stirring at temperature ranging between 30-40° C. until the solution becomes homogeneous;
   (e) mixing solution as prepared in step (d) with the solution as prepared in (c) dropwise and stirring for a period ranging between 30-120 minute at temperature ranging between 30-40° C. followed by adding hydrazine and stirring for 1-2 h at 30-40° C. and subsequently evaporating to dryness at 60-100° C. and further drying at 100-120° C. for 4-12 h then calcing in air atmosphere for 4-6 h at 450-750° C. to obtain nanocrystalline Pt—Ce oxide catalyst.

2. A process as claimed in claim 1, wherein the salt of Ce, surfactant and water are mixed in mol ratio range of 1:0.00008:20 to 1:0.00013:30 with constant stirring for 2-4 h at 40° C.

3. A process as claimed in claim 1, wherein the salt of Ce, surfactant and water in step (a) are mixed in mol ratio of 1:0.0001:24.78.

4. A process as claimed in claim 1, wherein Ce salt used in step (a) is $Ce(NO_3)_3 \cdot 6H_2O$.

5. A process as claimed in claim 1, wherein surfactant used in step (a) is Poly(diallyldimethylammonium chloride) solution (PDADMAC).

6. A process as claimed in claim 1, wherein molar ratio of Pt to CTAB in step (d) is in the range of 0.75-1.3.

7. A process as claimed in claim 1, wherein Pt to $CeO_2$ is in the range between 1 to 4 wt %.

8. A process as claimed in claim 1, wherein molar ratio of Pt to hydrazine is in the range of 0.75-4.

9. Nanocrystalline Pt—Ce oxide catalyst, produced by
   (a) mixing a salt of Cerium (Ce), a surfactant and water, with constant stirring for 2-4 h at a range of 35-45° C. while maintaining pH in the range of 8-9 to obtain a gel and further solidifying the gel by autoclaving the gel at temperature ranging between 150-180° C. for 7-10 days to obtain a solid;
   (b) filtering out and washing the solid as obtained in step (a) with ethanol and drying in an oven at a temperature range of 100-120° C. for a period ranging between 6-18 h followed by calcining the dried product at temperature range of 450-750° C. for a period ranging between 4-10 h to obtain Ce oxide;
   (c) preparing a solution by stirring Ce oxide as obtained in step (b) in ethanol for a period ranging between 30-120 min at temperature ranging between 30-40° C.;
   (d) preparing second solution by stirring ethanol, water, CTAB (cetyltrimethyl ammonium bromide) and platinum (Pt) salt by stirring at temperature ranging between 30-40° C. until the solution becomes homogeneous; and
   (e) mixing solution as prepared in step (d) with the solution as prepared in (c) dropwise and stirring for a period ranging between 30-120 minute at temperature ranging between 30-40° C. followed by adding hydrazine and stirring for 1-2 h at 30-40° C. and subsequently evaporating to dryness at 60-100° C. and further drying at 100-120° C. for 4-12 h then calcing in air atmosphere for 4-6 h at 450-750° C. to obtain nanocrystalline Pt—Ce oxide catalyst,
   where the particle size of $CeO_2$ lies between 20-50 nm and Pt-species with an average particle size of 1-3 nm with spherical nature catalyst and the Pt—Ce oxide catalyst comprises 1-4 wt % Pt and 99-96 wt % $CeO_2$.

10. A process for hydrogenation of phenol using nanocrystalline Pt—Ce oxide catalyst as obtained in process as claimed in claim 1 comprising placing pre-reduced nanocrystalline Pt—Ce oxide catalyst at 5-10% $H_2$ flow, water and phenol or substituted phenol substrate at 450-550° C. for 1-2h, wherein substrate to catalyst weight ratio varies between 100 to 1000 in a batch reactor followed by pressurizing the reactor with $H_2$ at pressure in the range of 1-3 MPa at temperature ranging between 100 –200° C. for a period ranging between 1-3 h to obtain cyclohexanol or substituted cyclohexanol.

11. A process as claimed in claim 10, wherein conversion of phenol or substituted phenol is in the range of 50-100%.

12. A process as claimed in claim 10, wherein selectivity of cyclohexanol or substituted cyclohexanol is in the range of 63-100%.

* * * * *